(12) United States Patent
Cheng et al.

(10) Patent No.: US 8,837,862 B2
(45) Date of Patent: Sep. 16, 2014

(54) IMAGE STITCHING METHOD AND CAMERA SYSTEM

(71) Applicant: Altek Corporation, Hsinchu (TW)

(72) Inventors: Shin-Hao Cheng, Taichung (TW); Pin-Wen Chen, Changhua County (TW)

(73) Assignee: Altek Corporation, Hsinchu (TW)

( * ) Notice: Subject to any disclaimer, the term of this patent is extended or adjusted under 35 U.S.C. 154(b) by 103 days.

(21) Appl. No.: 13/740,263

(22) Filed: Jan. 14, 2013

(65) Prior Publication Data

US 2014/0198298 A1  Jul. 17, 2014

(51) Int. Cl.
*G06K 9/32* (2006.01)
*A61B 3/14* (2006.01)

(52) U.S. Cl.
CPC ........................................ *A61B 3/14* (2013.01)
USPC ........................... 382/294; 348/135; 351/200

(58) Field of Classification Search
CPC ........ A61B 3/102; A61B 3/14; A61B 5/0066; A61B 3/12; A61B 3/1233; A61B 3/1241; A61B 3/0025; A61B 5/0261; G01B 9/02091; G01B 9/0203; G06K 9/00597; G06K 9/40; G06K 9/46; G06K 9/00281; G06K 9/20; G06K 9/6202; G02B 21/0028; G06T 7/0012; G06T 2207/10101; G06T 2207/30004
USPC ......... 382/100, 117, 154, 169, 170, 181, 190, 382/195, 254, 274, 275, 294; 378/4–27; 345/648, 672–688, 20, 63, 77, 345/581–618, 690, 697; 348/251, 254, 92, 348/135; 351/200–247

See application file for complete search history.

(56) References Cited

U.S. PATENT DOCUMENTS

| | | | |
|---|---|---|---|
| 5,615,278 A | 3/1997 | Matsumoto | |
| 7,648,239 B2* | 1/2010 | Spaide | 351/206 |
| 7,856,135 B1* | 12/2010 | Bernardes | 382/131 |
| 8,092,020 B2* | 1/2012 | Kolanko et al. | 351/205 |
| 8,260,084 B2* | 9/2012 | Wang et al. | 382/284 |
| 8,355,566 B2* | 1/2013 | Ng | 382/162 |
| 2002/0163530 A1* | 11/2002 | Takakura et al. | 345/629 |
| 2002/0176619 A1* | 11/2002 | Love | 382/154 |
| 2010/0195932 A1* | 8/2010 | Wang et al. | 382/284 |
| 2012/0075584 A1* | 3/2012 | Stetson | 351/206 |
| 2012/0157820 A1* | 6/2012 | Zhang et al. | 600/407 |

FOREIGN PATENT DOCUMENTS

| | | |
|---|---|---|
| TW | 201137787 | 11/2011 |
| TW | 201216204 | 4/2012 |

\* cited by examiner

*Primary Examiner* — Anand Bhatnagar
(74) *Attorney, Agent, or Firm* — Jianq Chyun IP Office (57) ABSTRACT

An image stitching method adapted to stitch a plurality of fundus images of an animal is provided. The image stitching method includes following steps. A plurality of fundus images of the animal are captured, where the fundus images partially overlap. The fundus images are respectively converted into a plurality of grayscale images. The contrasts of the grayscale images are enhanced. The grayscale images with enhanced contrasts are compared to obtain a plurality of stitching data. The fundus images are stitched according to the stitching data. Additionally, a camera system is also provided.

18 Claims, 10 Drawing Sheets

IMAGE STITCHING METHOD AND CAMERA SYSTEM

BACKGROUND OF THE INVENTION

1. Field of the Invention

The invention generally relates to an image processing method and an optical system, and more particularly, to a method of stitching fundus images of an eye of an animal and a camera system.

2. Description of Related Art

Eyes are the window to the soul, and people see the world through their eyes. The cone and rod cells responsible for color and light reception in the eye are located in the retina at the fundus and are the photoreceptors for converting light into physiological electrical signals in the human body. The blood vessels for supplying blood and nutrients to the eye are also located at the fundus. When a vascular hyperplasia or rupture occurs on the fundus (for example, macular degeneration), the cone and rod cells in the retina may die and accordingly the patient may lose his or her eyesight. Thus, it is very important to observe and track fundus images in the diagnosis and prevention of eye diseases.

Generally, due to the limitation in the size of human pupil, the conventional fundus image capturing technique can capture a fundus image within a range of about 30° to 40° from each shooting angle. Thus, to capture images of the brim of the fundus, the patient has to stare at a reference point and then move his or her eyes around the reference point at a slow and steady speed. Through this technique, a plurality of fundus images can be captured. After that, the fundus images are merged by using a data processing apparatus (for example, a computer) and a special image synthesis software. However, because these fundus images are not captured all together, they have different exposure values and white balance values. In addition, the fundus images need to be corrected before they are stitched, which causes the correction of the fundus images to be complicated and the quality of the stitched image to be reduced. With the reduced quality of the stitched image, capillary vessels may be difficult to identify and accordingly diagnosis may not be made or the best treatment timing may even be missed out. Thereby, how to obtain complete and clear fundus images in a short time is a major subject in the medical industry.

SUMMARY OF THE INVENTION

Accordingly, the invention is directed to an image stitching method, in which the accuracy of image stitching is improved.

The invention is directed to a camera system offering an accurate image stitching effect.

An embodiment of the invention provides an image stitching method adapted to stitch a plurality of images of a fundus of an eye of an animal. The image stitching method includes following steps. A plurality of fundus images of the eye of the animal are captured, where the fundus images partially overlap. The fundus images are respectively converted into a plurality of grayscale images. The contrasts of the grayscale images are enhanced. The grayscale images with enhanced contrasts are compared to obtain a plurality of stitching data. The fundus images are stitched according to the stitching data.

According to an embodiment of the invention, the step of capturing the fundus images includes capturing the fundus images by using an optical lens, and before the step of respectively converting the fundus images into the grayscale images, the image stitching method further includes correcting the fundus images according to an optical parameter of the optical lens, where the step of respectively converting the fundus images into the grayscale images includes respectively converting the corrected fundus images into the grayscale images.

According to an embodiment of the invention, the step of correcting the fundus images includes diminishing pincushion distortion of the fundus images.

According to an embodiment of the invention, the fundus images are color images.

According to an embodiment of the invention, the step of enhancing the contrast of each grayscale image further includes following steps. A grayscale distribution relation between a pixel number and a grayscale value in the grayscale image is calculated. A grayscale range corresponding to a section having a greatest continuous slope variation in the grayscale distribution relation is served as a pending grayscale range. A converting relation between the pending grayscale range and a contrast-enhanced grayscale range is determined, where the lower limit of the contrast-enhanced grayscale range is smaller than the lower limit of the pending grayscale range, and the upper limit of the contrast-enhanced grayscale range is greater than the upper limit of the pending grayscale range. A plurality of grayscale values corresponding to the pending grayscale range in the grayscale image is respectively converted into a plurality of grayscale values of the contrast-enhanced grayscale range according to the converting relation.

According to an embodiment of the invention, the step of comparing the grayscale images with the enhanced contrasts to obtain the stitching data includes executing a planar surface stitching algorithm on the grayscale images with the enhanced contrasts to calculate the stitching data, wherein the stitching data includes a plurality of stitching data respectively corresponding to the fundus images.

According to an embodiment of the invention, at least a part of the fundus images includes at least one of an optic disc image, a macula image, and a blood vessel image, and the step of comparing the grayscale images with the enhanced contrasts to obtain the stitching data includes comparing a part of the grayscale images with the enhanced contrasts corresponding to at least one of the optic disc image, the macula image, and the blood vessel image on a first priority to obtain the stitching data.

According to an embodiment of the invention, the step of capturing the fundus images of the animal includes capturing the fundus images of the animal from a plurality of different angles.

An embodiment of the invention provides a camera system adapted to capture a plurality of images of a fundus of an eye of an animal. The camera system includes a camera unit and a processing unit. The camera unit captures a plurality of fundus images of the eye of the animal, where the fundus images partially overlap. The processing unit is electrically connected with the camera unit. The processing unit respectively converts the fundus images into a plurality of grayscale images. The processing unit enhances the contrasts of the grayscale images. The processing unit compares the grayscale images with the enhanced contrasts to obtain a plurality of stitching data. The processing unit stitches the fundus images according to the stitching data.

According to an embodiment of the invention, the camera unit includes an optical lens and an image sensor. The camera unit aims at the fundus of the animal from a plurality of different angles, so that the optical lens projects the fundus on the image sensor from the different angles and the image sensor respectively captures the fundus images.

According to an embodiment of the invention, the camera system further includes an actuator, wherein the actuator is connected to the camera unit for moving the camera unit to the different angles.

According to an embodiment of the invention, the processing unit corrects the fundus images according to an optical parameter of the optical lens and then respectively converts the corrected fundus images into the grayscale images.

According to an embodiment of the invention, the processing unit diminishes pincushion distortion of the fundus images according to the optical parameter of the optical lens.

According to an embodiment of the invention, the fundus images are color images.

According to an embodiment of the invention, the processing unit calculates a grayscale distribution relation between a pixel number and a grayscale value in each of the grayscale images, the processing unit serves a grayscale range corresponding to a section having the greatest continuous slope variation in the grayscale distribution relation as a pending grayscale range, the processing unit determines a converting relation between the pending grayscale range and a contrast-enhanced grayscale range, the lower limit of the contrast-enhanced grayscale range is smaller than the lower limit of the pending grayscale range, the upper limit of the contrast-enhanced grayscale range is greater than the upper limit of the pending grayscale range, and the processing unit respectively converts a plurality of grayscale values corresponding to the pending grayscale range in the grayscale image into a plurality of grayscale values of the contrast-enhanced grayscale range according to the converting relation.

According to an embodiment of the invention, at least a part of the fundus images includes at least one of an optic disc image, a macula image, and a blood vessel image, and the processing unit compares a part of the grayscale images with the enhanced contrasts corresponding to at least one of the optic disc image, the macula image, and the blood vessel image on a first priority to obtain the stitching data.

According to an embodiment of the invention, the camera system further includes an illumination light source for providing an illumination beam to the fundus of the animal, wherein the fundus reflects the illumination beam into a plurality of image beams respectively carrying the fundus images, and the camera unit is respectively disposed on light paths of the image beams at a plurality of different time points for capturing the fundus images.

As described above, in an image stitching method and a camera system provided by embodiments of the invention, a plurality of fundus images is captured and converted into a plurality of grayscale images, the contrasts of the grayscale images are enhanced, stitching data is calculated according to the grayscale images with the enhanced contrasts, and the fundus images are stitched according to the stitching data. Thereby, the time for stitching the fundus images is shortened, and the accuracy in the stitching of the fundus images and the quality of the stitched image are improved to provide a fundus image with a wide viewing angle.

These and other exemplary embodiments, features, aspects, and advantages of the invention will be described and become more apparent from the detailed description of exemplary embodiments when read in conjunction with accompanying drawings.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

Figure 1A:
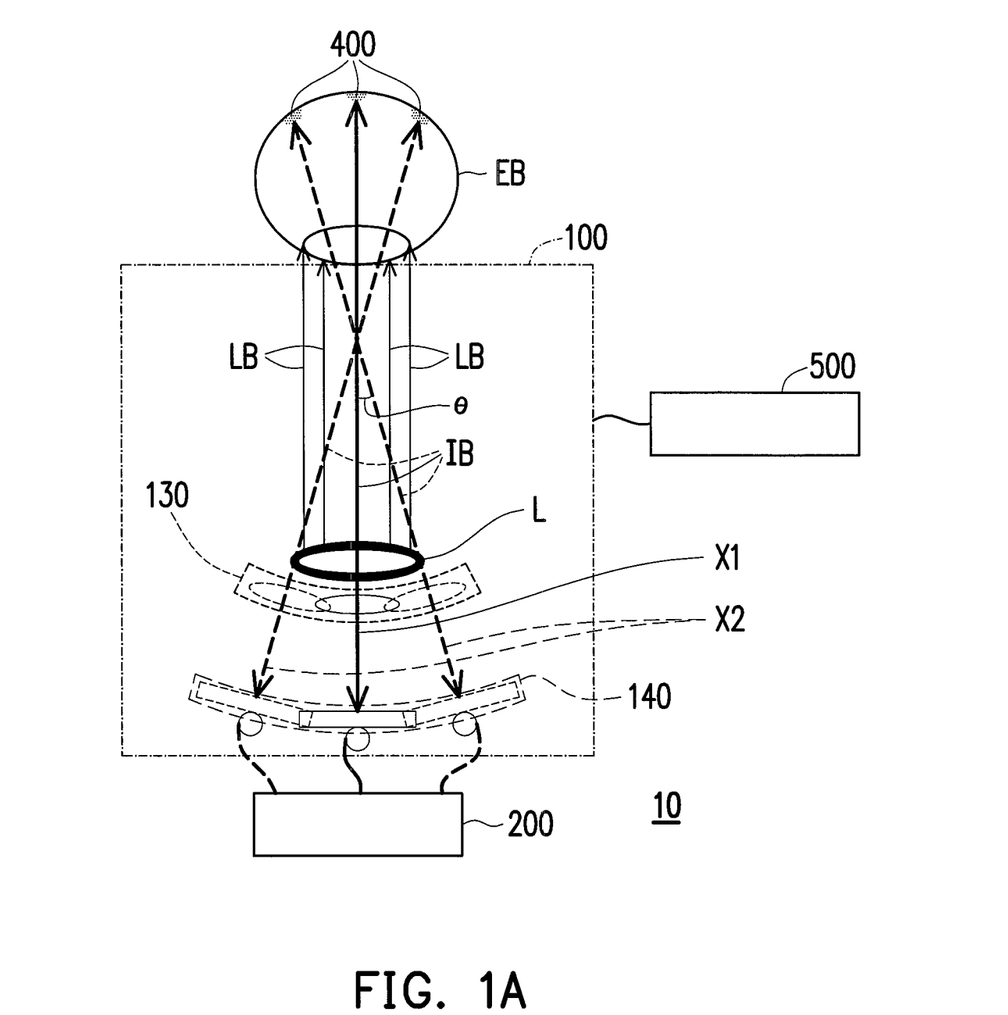
FIG. 1A is a diagram of a camera system according to an embodiment of the invention.

FIG. 1A is a diagram of a camera system according to an embodiment of the invention. Referring to FIG. 1A, in the present embodiment, the camera system 10 includes a camera unit 100 and a processing unit 200. The camera unit 100 captures a plurality of fundus images 400 of an animal (i.e. images of the fundus of the eye of the animal), where the fundus images 400 partially overlap each other. In the present embodiment, the fundus images 400 are full-color images. However, the invention is not limited thereto, and in other embodiments, the fundus images 400 may also be color or grayscale images obtained through infrared photography or any other technique. The processing unit 200 is electrically connected with the camera unit 100. The processing unit 200 respectively converts the full-color fundus images 400 into a plurality of grayscale fundus images 400G (as shown in FIG. 3C) and enhances the contrasts of the grayscale fundus images 400G into contrast-enhanced grayscale fundus images 400GE (as shown in FIG. 3D). Herein the processing unit 200 may be an application-specific integrated circuit (ASIC). Thereafter, a plurality of stitching data is calculated according to the enhanced grayscale fundus images 400GE, and the full color fundus images 400 are stitched according to the stitching data.

To be specific, in the present embodiment, the camera unit 100 further includes an optical lens 130 and an image sensor 140. The image sensor 140 may be a charge coupled device (CCD), a complementary metal-oxide-semiconductor (CMOS) sensing device, or any other photosensitive device. Before the processing unit 200 converts the fundus images 400 into the grayscale images 400G, the processing unit 200 corrects the fundus images 400 according to an optical parameter of the optical lens 130. The optical parameter includes at least one of distortion, aberration, chromatic aberration, and any other optical parameter. Because these optical parameters can be obtained by measuring the optical lens 130 and the approximate curvature of the fundus is known, the fundus images can be corrected to obtain a plurality of planar fundus images 400. Thus, the processing unit 200 in the present embodiment can effectively improve the efficiency and accuracy of subsequent stitching operation and facilitate the diagnosis of medical staff.

In addition, the camera system 10 includes an illumination light source L. The illumination light source L provides an illumination beam LB to the fundus of the eye EB. The fundus of the eye EB reflects the illumination beam LB into a plurality of image beams LB respectively carrying the fundus images. The camera unit 100 is respectively positioned on the light paths of the image beams LB at a plurality of different time points to capture the fundus images 400. In the embodiment illustrated in FIG. 1A, the illumination light source L is a circular light source disposed between the eye EB and the optical lens 130. However, the invention is not limited thereto, and in other embodiments, the illumination light source L may also be disposed at other positions.

Moreover, in the present embodiment, the camera system 10 further includes a control unit 500 electrically connected with the camera unit 100. The eye EB has a first optical axis X1, and the camera unit 100 has a second optical axis X2. The control unit 500 changes the angle θ between the second optical axis X2 and the first optical axis X1 to capture the fundus images 400 from a plurality of different angles. Accordingly, the fundus images 400 within a wide viewing angle range can be captured through a single shooting action and can have very similar exposure values and white balance values. Thus, the viewing angle of the fundus images 400 is widened and the quality thereof is improved, and accordingly the accuracy of clinical diagnosis is improved.

Figure 1B:
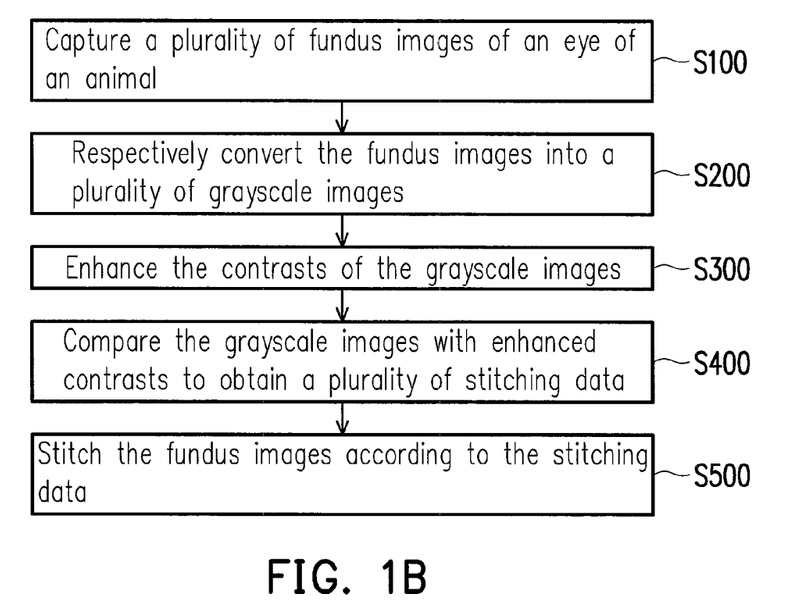
FIG. 1B is a flowchart of an image stitching method according to an embodiment of the invention.
Figure 1C:
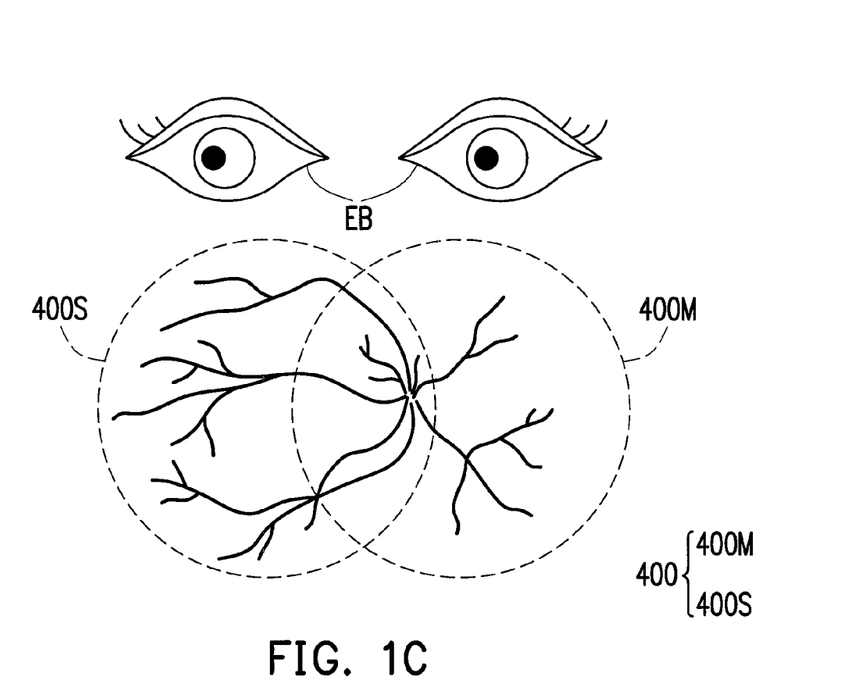
FIG. 1C is a diagram illustrating how fundus images are captured from different angles in step S100 in the embodiment illustrated in FIG. 1B.

FIG. 1B is a flowchart of an image stitching method according to an embodiment of the invention. FIG. 1C is a diagram illustrating how fundus images are captured from different angles in step S100 in the embodiment illustrated in FIG. 1B. Referring to FIG. 1B and FIG. 1C, the image stitching method in the present embodiment can be accomplished by the camera system 10 illustrated in FIG. 1A. In the present embodiment, the image stitching method includes following steps. First, a plurality of fundus images 400 of an animal is captured (step S100). For example, as shown in FIG. 1C, full-color fundus images 400 (including a fundus image 400M captured from the front viewing angle of the eye EB and a fundus image 400S captured from an angle relative to the eye EB) of a human eye are captured from different angles. These fundus images 400 partially overlap. Thereafter, the fundus images 400 are respectively converted into a plurality of grayscale images 400G (step 200). For example, the fundus images 400 are converted into grayscale images 400G by the processing unit 200 in FIG. 1A. The, the contrasts of the grayscale images 400G are enhanced (step 300) to enhance the pathological feature (for example, the distribution of capillaries or the color of macular tissue). Besides, the grayscale images 400GE with enhanced contrasts are compared to obtain a plurality of stitching data (step S400). For example, by enhancing the contrasts of the grayscale images 400G through the processing unit 200 in FIG. 1A, image features (for example, capillaries or macula) can be enhanced, and relations between the images can be calculated according to these image features, so that subsequently the images can be successfully stitched. After that, the fundus images 400 are stitched according to the stitching data (step S500). By converting the fundus images 400G into the grayscale images 400Ge and enhances the image features thereof, the time for stitching the fundus images 400 and the error rate of the stitching operation are effectively reduced compared to directly stitching the full-color fundus images 400. Besides, by capturing the fundus images 400 from different angles, the viewing angle of the stitched image is wider than that (ranges from about 30° to about 40°) of a fundus image captured by a single shot through the conventional technique, and accordingly the diagnosis of any fundus disease is made easier. It should be mentioned that the numbers of the fundus images 400, 400M, and 400S in the present embodiment are only examples and not intended to limit the scope of the invention, and the fundus images may also be continuously captured in other embodiments.

Figure 2A:
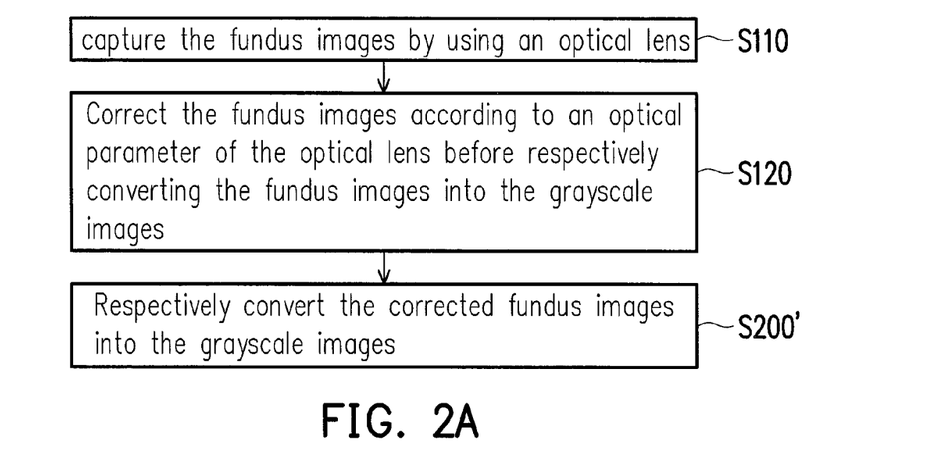
FIG. 2A is a detailed flowchart of steps S100-S200 in the embodiment illustrated in FIG. 1A.

FIG. 2A is a detailed flowchart of steps S100-S200 in the embodiment illustrated in FIG. 1A. Referring to FIG. 2A, the step of capturing the fundus images 400 (step S100) includes capturing the fundus images 400 by using the optical lens 130 (step S110). Because the fundus is a concave surface with certain diopter, the fundus images 400 captured through the optical lens 130 may come with image distortion (for example, pincushion distortion). Thus, before respectively converting the fundus images 400 into the grayscale images 400G, the fundus images 400 are corrected according to an optical parameter of the optical lens 130 (step S120). Accordingly, image distortion to be dealt with in subsequent stitching operation can be eliminated. Thereafter, the corrected fundus images 400 are respectively converted into the grayscale images 400G (step S200'). For example, each fundus image 400 has a plurality of image spots, and each image spot has a first color information CR, a second color information CG, and a third color information CB. To be specific, the fundus images 400 can be converted into the grayscale images 400G by using following algorithm:

$G=F(CR,CG,CB)$, wherein $F$ is a function.

To be specific, the first color information CR, the second color information CG, and the third color information CB can be brought into a grayscale function G as following:

$$G = \frac{[(9798 \cdot CR) + (19235 \cdot CG) + (3735 \cdot CB)]}{32768}.$$

Namely, the first color information CR, the second color information CG, and the third color information CB of each image spot in a full-color fundus image 400 can be converted into a grayscale image 400G by using foregoing algorithm. Thus, in the present embodiment, the full-color fundus images 400 captured in FIG. 1C from different angles can be converted into grayscale fundus images 400G. Additionally, the original full-color fundus images 400 are retained for subsequent processing after the distortion thereof are corrected according to an optical parameter of the optical lens 130.

Figure 2B:
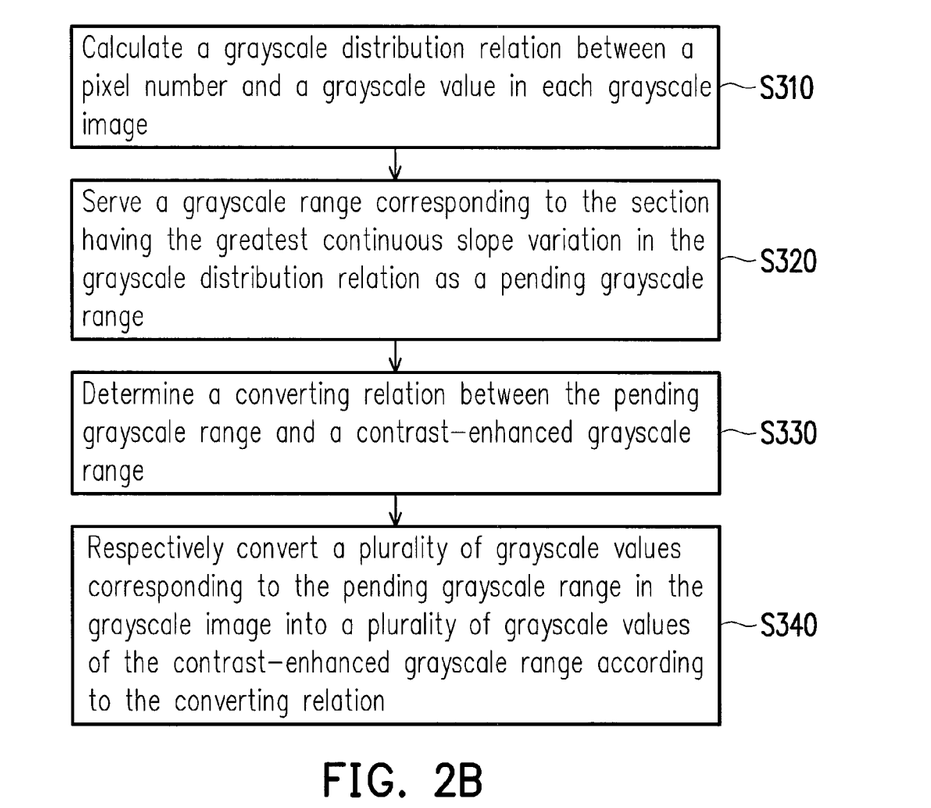
FIG. 2B is a detailed flowchart of a step S300 in the embodiment illustrated in FIG. 1A.

FIG. 2B is a detailed flowchart of a step S300 in the embodiment illustrated in FIG. 1A. Referring to FIG. 2B, in the step (step S300) of enhancing the contrast of each grayscale image 400G, a grayscale distribution relation between a pixel number and a grayscale value in the grayscale image 400G is calculated (step S310). Then, a grayscale range corresponding to the section having the greatest continuous slope variation in the grayscale distribution relation is served as a pending grayscale range (step S320). Next, a converting relation between the pending grayscale range and a contrast-enhanced grayscale range is determined (step S330). Herein the lower limit of the contrast-enhanced grayscale range is smaller than the lower limit of the pending grayscale range, and the upper limit of the contrast-enhanced grayscale range is greater than the upper limit of the pending grayscale range. Besides, a plurality of grayscale values corresponding to the pending grayscale range in the grayscale image 400G is respectively converted into a plurality of grayscale values of the contrast-enhanced grayscale range according to the converting relation (step S340). Namely, the contrast-enhanced grayscale range is greater than the pending grayscale range in the grayscale distribution. In other words, the converting relation allows the densely distributed grayscale images 400G to be appropriately converted into the sparsely distributed grayscale images 400GE. Thereby, the contrasts of the grayscale images are enhanced and the features (for example, the distribution of capillaries or the state of the macula) of the fundus images are emphasized, so that the subsequent image stitching operation and clinical diagnosis can be facilitated.

Figure 3A:
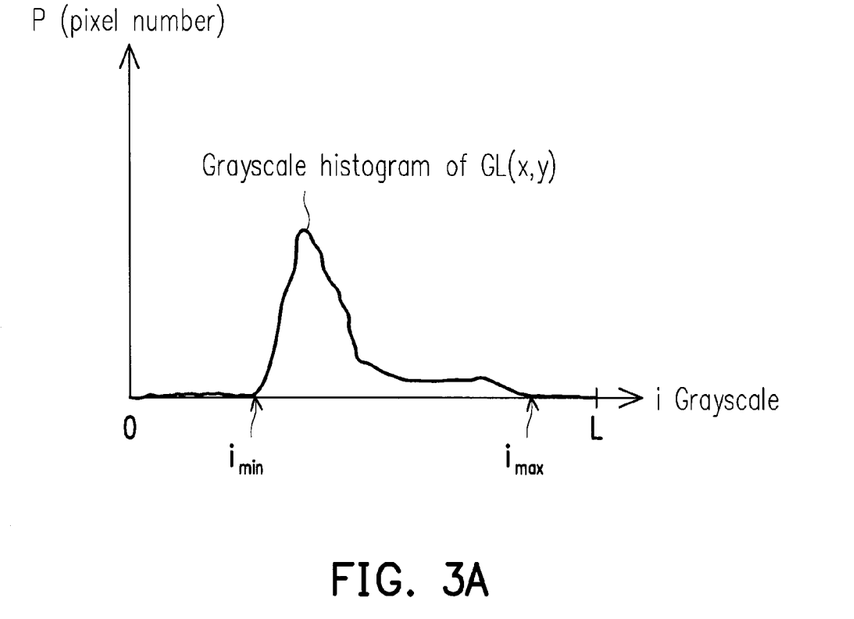
FIG. 3A is a grayscale histogram of a grayscale function GL of grayscale fundus images 400G according to step S320 in FIG. 2B.
Figure 3B:
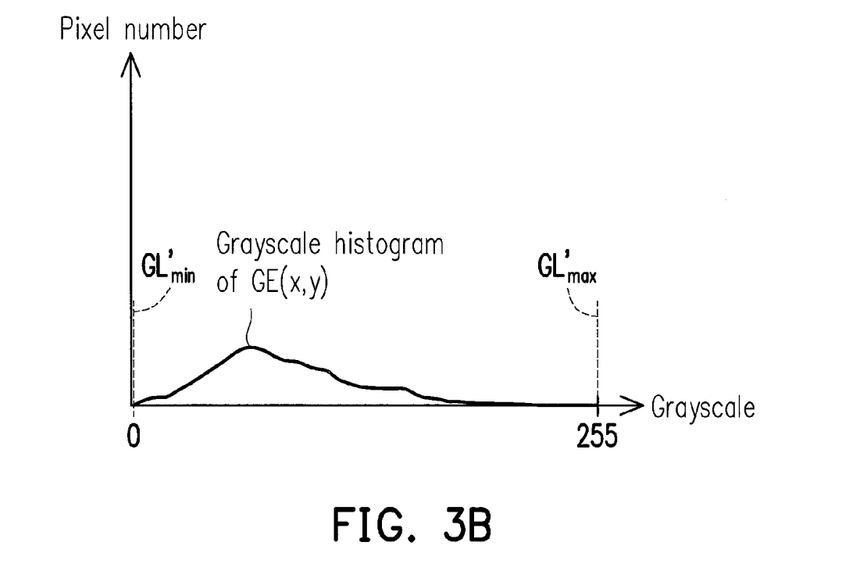
FIG. 3B is a grayscale histogram of a grayscale function GE of grayscale fundus images 400GE according to step S320 in FIG. 2B.
Figure 3C:
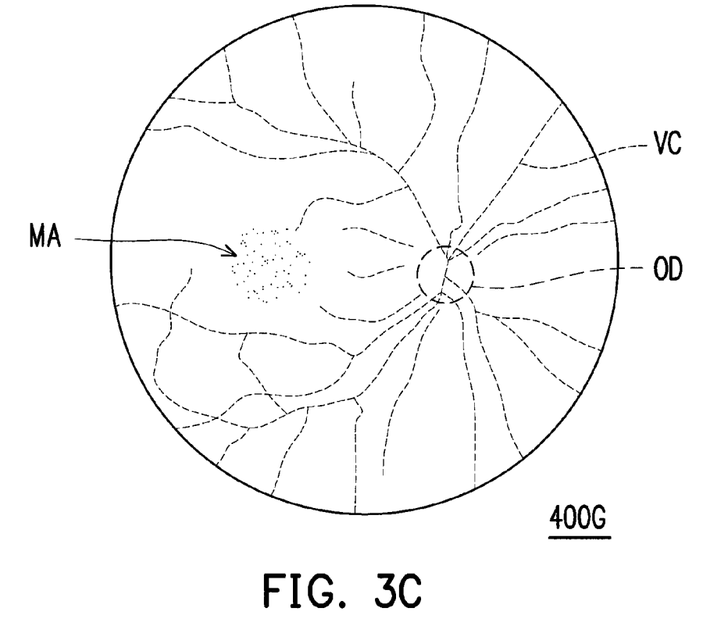
FIG. 3C is a diagram of a grayscale image 400G in FIG. 3A.
Figure 3D:
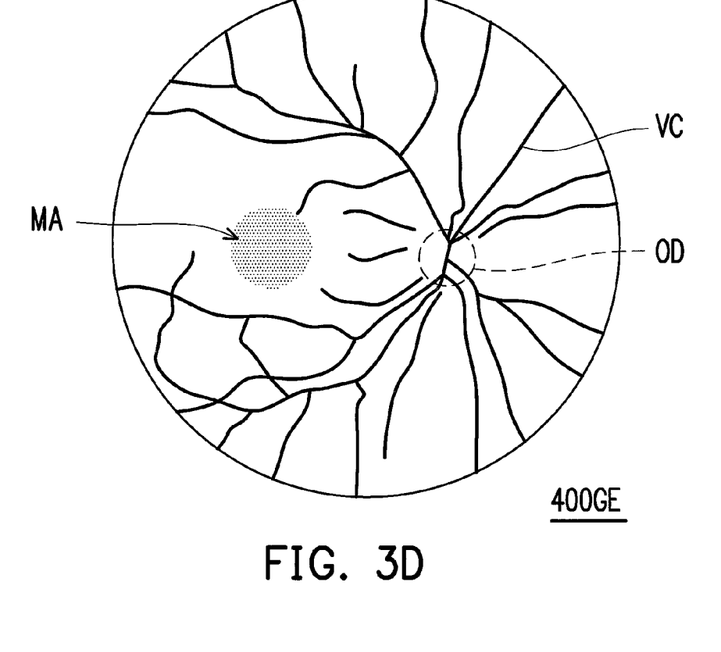
FIG. 3D is a diagram of a grayscale image 400GE in FIG. 3B.

FIG. 3A is a grayscale histogram of a grayscale function GL of grayscale fundus images 400G according to step S320 in FIG. 2B. FIG. 3B is a grayscale histogram of a grayscale function GE of grayscale fundus images 400GE according to step S320 in FIG. 2B. Referring to FIG. 3A and FIG. 3B, in the present embodiment, each fundus image 400G can be converted into a L-level grayscale fundus image GL(x,y) by calculating the grayscale value of each pixel in the fundus image 400G, where x and y respectively represent the values of the fundus image GL(x,y) on the axis x and the axis y (i.e., corresponding to the position of each pixel). The grayscale histogram generated based on the grayscales of the pixels in each grayscale fundus image 400G (i.e., generated based on the fundus image GL(x, y)) can be expressed as following:

$$P_{cummulate}(GL) = \sum_{i=0}^{L} P(i)$$

In foregoing equation, $P_{cummulate}(GL)$ represents the total number of pixels in the fundus image GL(x,y), L represents the maximum grayscale value in the grayscale histogram of the fundus image GL(x,y), i represents the grayscale value (i.e., the abscissa in FIG. 3A), and P(i) represents the number of pixels having the grayscale value i. Thus, the fundus image GL(x,y) can be converted into the grayscale histogram illustrated in FIG. 3A. After that, the section of the grayscale histogram in which P(i) is not zero (for example, the range from i=k to i=k+n) is selected to calculate following equation:

$$Psum = \sum_{i=k}^{k+n} |P(i+1) - P(i)|$$

Next, the section having the maximum Psum (for example, the section from $i=i_{min}$ to $i=i_{max}$) is selected and brought into a linear conversion equation, and the section from $i_{min}$ to $i_{max}$ in the grayscale histogram is extended to enhance the image contrast. The linear conversion equation mentioned above is as following:

$$GE(x, y) = INT\left\{ \frac{(GL'\max - GL'\min)}{i_{max} - i_{min}} [GL(x, y) - i_{min}] + GL'\min \right\}$$

In foregoing equation, INT{ } is a function returning integer, and GL'max and GL'min respectively represent the maximum and minimum grayscale values in the grayscale histogram of the fundus image GE(x,y). Thus, in the step of determining the converting relation between the pending grayscale range and the contrast-enhanced grayscale range (step S330), the grayscale image GL(x,y) of each grayscale image 400G can be converted into a function GE(x,y) to obtain an enhanced grayscale image. Herein GL'min is a value greater than or equal to 0. For example, the value of GL'max may be 255 (i.e., the maximum of 8-bit grayscale value common in image processing), and the value of GL'min is 0, such that the grayscale distribution range of the grayscale image 400G to be converted is extended to 255 and the contrast thereof is enhanced. However, the invention is not limited thereto, and in other embodiments, the values of GL'min and GL'max can be determined according to the actual requirement to achieve a fundus image quality most suitable for diagnosis. Additionally, in foregoing equation, the grayscale range from $i_{min}$ to $i_{max}$ is evenly expanded. In other embodiments, to obtain grayscale images most suitable for stitching (for example, images with great contrast between blood vessels and surrounding tissues), a gamma or another type of correction may be performed on the grayscale values (equivalent to expanding the grayscale values between $i_{min}$ and $i_{max}$ in an uneven manner). Thereafter, a plurality of grayscale values corresponding to the pending grayscale range in the grayscale image 400G is respectively converted into a plurality of grayscale values of the contrast-enhanced grayscale range according to the converting relation (for example, foregoing conversion equation) (step S340). Namely, the contrasts of the grayscale images are enhanced through foregoing linear conversion equation to obtain the enhanced grayscale images. For example, in the present embodiment, the grayscale fundus images 400G are converted into the grayscale images 400GE, and the features (for example, the distribution of blood vessels VC or the macula MA) of the fundus images are then enhanced for the convenience of subsequent image stitching operation and clinical diagnosis.

FIG. 3C is a diagram of a grayscale image 400G in FIG. 3A. FIG. 3D is a diagram of a grayscale image 400GE in FIG. 3B. Referring to FIG. 3A, FIG. 3B, FIG. 3C, and FIG. 3D, the method of enhancing the grayscale images in step S300 is to capture the section having the greatest grayscale variation (for example, the grayscale range $i_{min}$ to $i_{max}$ in FIG. 3A) in the grayscale fundus image 400G, and the grayscale differences between grayscale pixel and grayscale pixel are enhanced to enhance the contrast of each grayscale pixel (for example, the grayscale range $i_{min}$ to $i_{max}$ in FIG. 3A can be extended to the grayscale range 0 to 255 in FIG. 3B). Thus, the contrast of the grayscale fundus image 400G (for example, the one in FIG. 3C) can be effectively enhanced to obtain the grayscale fundus image 400GE in FIG. 3D. Particularly, the part of the grayscale image corresponding to the optic disc (densely distributed with blood vessels) has greater grayscale difference than that of other peripheral parts of the grayscale image. Through the technique and algorithm described above, the contrast at the fringes of the blood vessels is enhanced through the algorithm described above. Thus, the medical staff can identify the blood vessels correctly. In other words, the accuracy and reliability of clinical diagnosis based on these enhanced fundus images are improved.

Figure 4A:
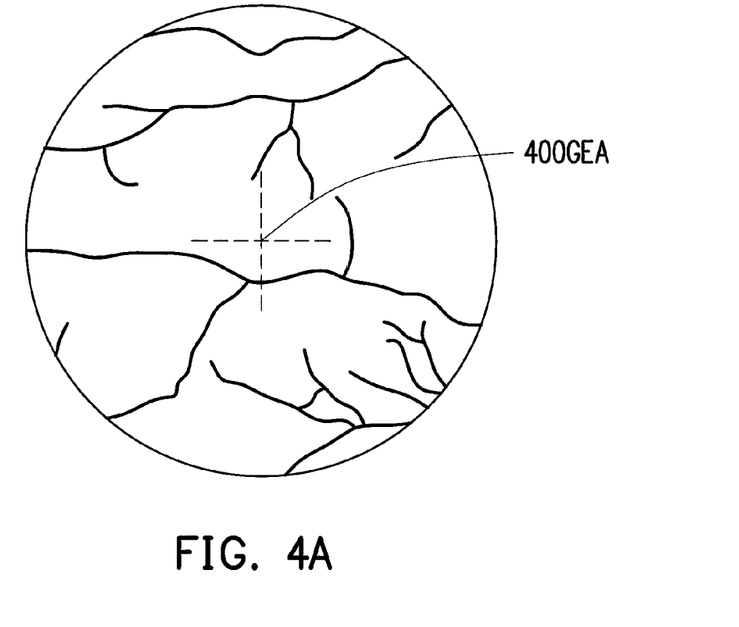
FIG. 4A is a diagram of an enhanced grayscale fundus image 400GE with a macula.
Figure 4B:
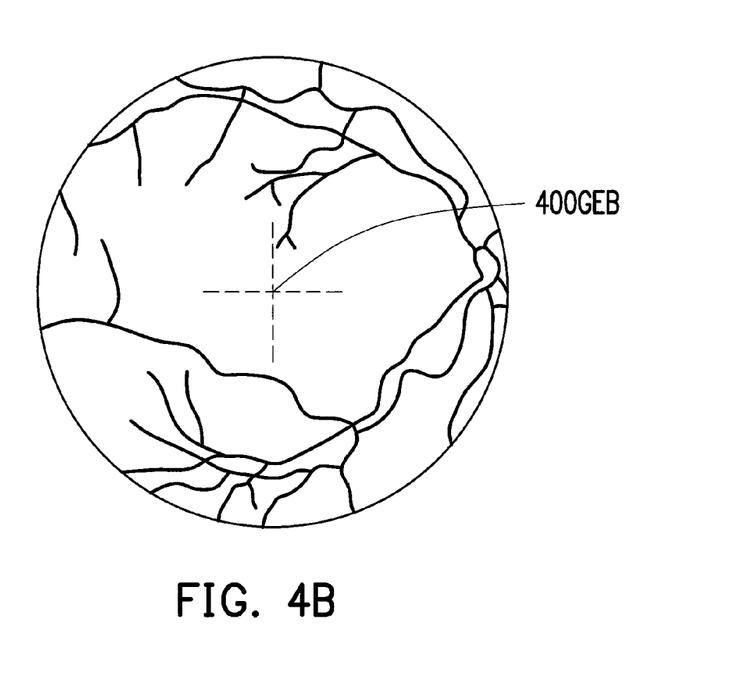
FIG. 4B is a diagram of an enhanced grayscale fundus image 400GE with an optic disc.
Figure 4C:
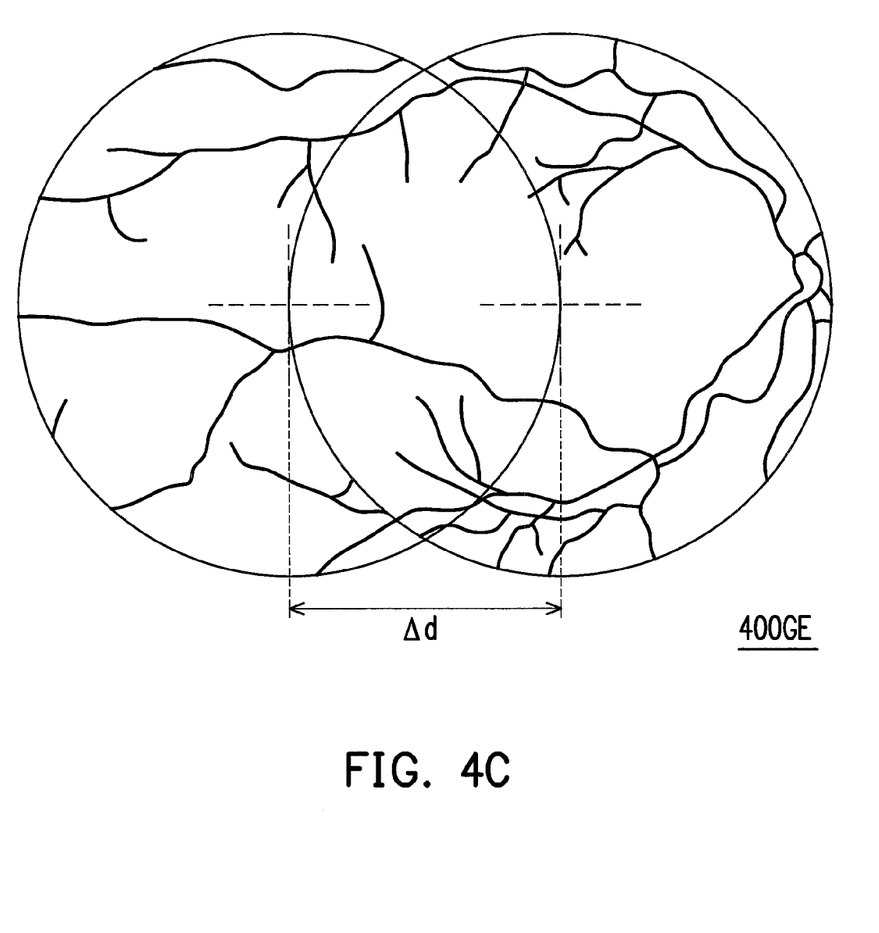
FIG. 4C is a diagram of a grayscale image 400GE obtained by stitching the fundus images in FIG. 4A and FIG. 4B according to stitching data.

FIG. 4A is a diagram of an enhanced grayscale fundus image 400GE with a macula. FIG. 4B is a diagram of an enhanced grayscale fundus image 400GE with an optic disc. FIG. 4C is a diagram of a grayscale image 400GE obtained by stitching the fundus images in FIG. 4A and FIG. 4B according to stitching data. Referring to FIG. 3C to FIG. 4C, in the step of comparing the grayscale fundus images 400GE with enhanced contrasts to obtain a plurality of stitching data (step S400), the stitching data between the fundus images 400GE can be calculated by using a planar surface stitching algorithm and the enhanced grayscale fundus images 400GE, where the stitching data includes a plurality of offsets Δd respectively corresponding to the fundus images 400GE. To be specific, referring to FIG. 1C first, the full-color fundus images 400 may be images of the part of the fundus close to the center of the fundus (for example, the fundus image 400M) or images of the part of the fundus away from the center of the fundus (for example, the fundus image 400S). Before step S200, the full-color fundus images 400 can be corrected according to the optical parameter of the optical lens 130 in FIG. 1A to eliminate distortion or aberration, so as to obtain planar surface images. After that, referring to FIG. 3C and FIG. 3D, the full-color fundus images 400 are converted into a plurality of planar grayscale fundus images 400G in step S200. Next, referring to FIGS. 4A-4C, regarding the grayscale fundus images 400GE enhanced through step S300 (for example, the grayscale fundus image 400GEA in FIG. 4A and the grayscale fundus image 400GEB in FIG. 4B), the offset Δd between the centers (for example, the dotted crosses in FIGS. 4A-4D) of the two grayscale fundus images can be identified by using a planar surface algorithm supported by an application-specific integrated circuit (ASIC). Herein the grayscale fundus images 400GEA and 400GEB in FIG. 4A and FIG. 4B respectively include the macula MA and the optic disc OD in FIG. 3C and FIG. 3D as examples for describing the present embodiment. However, the invention is not limited thereto, and in other embodiments, a plurality of continuously captured grayscale images 400GE may also be stitched.

Figure 4D:
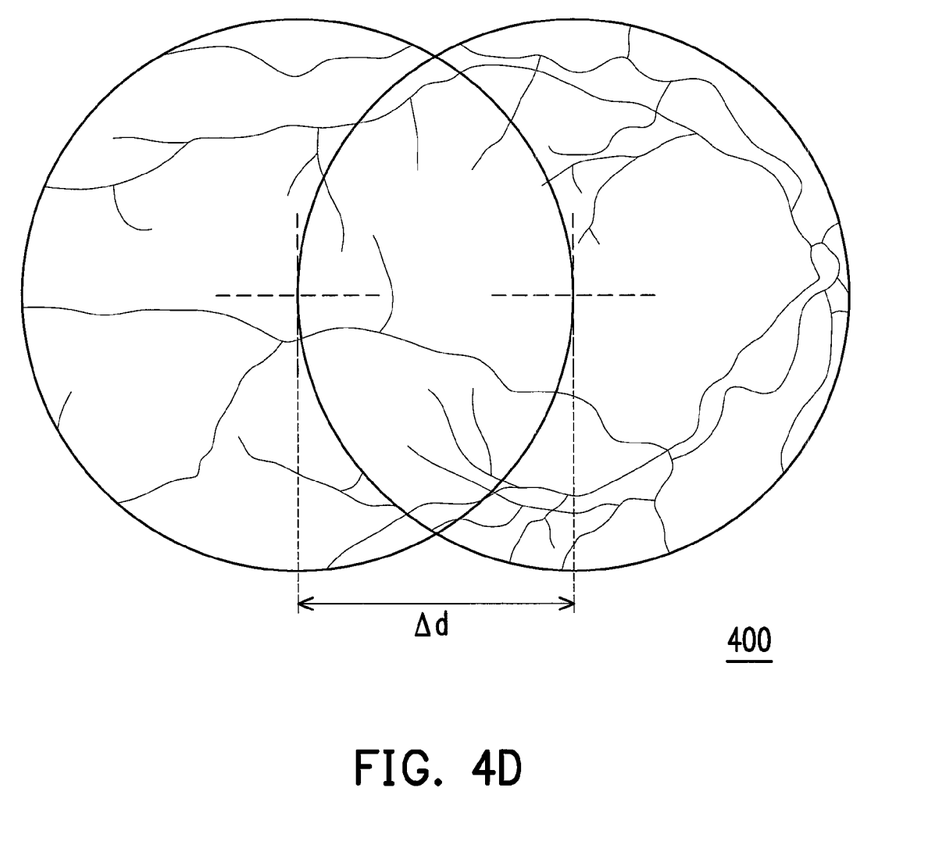
FIG. 4D is a diagram of an image obtained by stitching full color fundus images 400 according to the stitching data in FIG. 4C.

FIG. 4D is a diagram of an image obtained by stitching full color fundus images 400 according to the stitching data in FIG. 4C. Referring to FIG. 4D, while stitching the fundus images according to the stitching data (step S500), in the present embodiment, the offset Δd in the stitching data can be brought into two corresponding planar full-color fundus images 400 to merge the two planar full-color fundus images 400. In other embodiments, the offsets Δd between every two of a plurality of fundus images 400 may be calculated through the same technique, so that a full-color fundus image 400 of a wider viewing angle can be obtained. Generally, if the central positions of the full-color fundus images 400 are directly calculated to stitch a fundus image of a wider viewing angle, it may be difficult to identify the relative position of the capillaries due to color affection, so that the time for stitching the full-color fundus images 400 may be prolonged and stitching errors may be produced. In the present embodiment, the full-color fundus images 400 are first converted into the grayscale images 400G, and then the contrasts of the grayscale images 400G are enhanced to make the capillaries to be identified easily. Thus, the time for calculating the offsets Δd is shortened and the accuracy in the image stitching is improved. Thereafter, the offset Δd is brought into the full-color fundus images 400 to stitch the full-color fundus images 400, so that the accuracy and efficiency of the stitching operation won't be affected by the color.

Additionally, in the present embodiment, at least part of the fundus images 400 includes at least one of the images of the optic disc OD, the macula MA, and the blood vessel VC, such as the fundus image 400GEA in FIG. 4A that contains images of the optic disc OD and the blood vessel VC in FIG. 3C and FIG. 3D, and the fundus image 400GEB in FIG. 4B that contains images of the macula MA in FIG. 3C and FIG. 3D. The step of comparing the grayscale images 400GE with enhanced contrasts to obtain the stitching data includes comparing the part of the grayscale images 400GE with enhanced contrasts that is corresponding to at least one of the images of the optic disc OD, the macula MA, and the blood vessel VC on a first priority to obtain the stitching data. The macula MA displays a yellow color due to the densely distributed photoreceptor cells and lutein, and which is located at the central area of the retina and is one of the distinctive parts in the fundus images along with the optic disc OD (also called a blind spot) with densely distributed capillaries. Thus, by stitching fundus images based on the offset Δd of the image centers of the fundus images containing the images of the macula MA and the optic disc OD, the accuracy in the image stitching is improved. Besides, the important pathological fundus information (for example, the distribution of the blood vessel VC and the tissue color of the macula MA) carried by the fundus images can facilitate the observation and diagnosis of the medical staff.

Figure 5A:
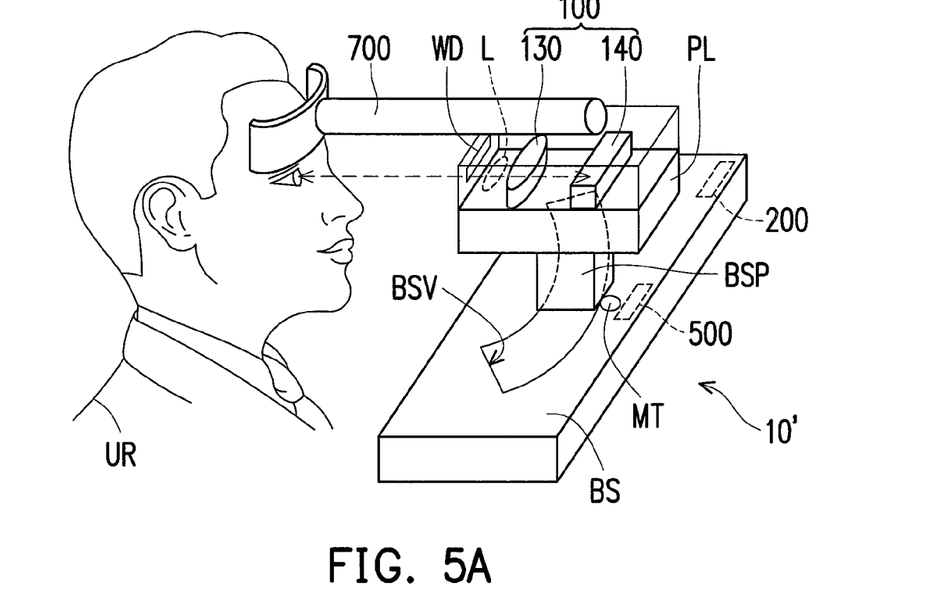
FIG. 5A is a diagram of a camera system according to another embodiment of the invention.
Figure 5B:
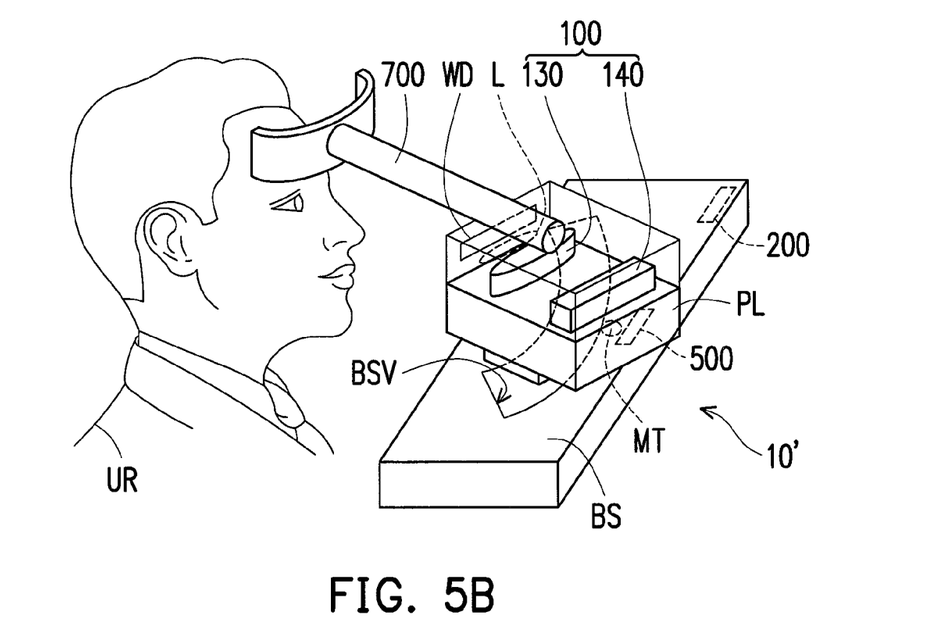
FIG. 5B is a diagram illustrating the operation of the camera system in FIG. 5A.

FIG. 5A is a diagram of a camera system according to another embodiment of the invention. FIG. 5B is a diagram illustrating the operation of the camera system in FIG. 5A. Referring to FIG. 5A and FIG. 5B, in the present embodiment, the camera system 10' has a base BS, a supporting portion BSP, and a platform PL. The base BS has a track BSV. The supporting portion BSP can slide in the track BSV. A camera unit 100 and an optical lens 130 are disposed in the platform PL. The supporting portion BSP is connected with and supports the platform PL. In addition, the camera system 10' also includes a supporting element 700 disposed above the platform PL. A user UR can lean his or her face against the supporting element 700 to maintain an appropriate distance to the optical lens 130 and the camera unit 100. The camera system 10' can quickly capture fundus images of the user UR through a window WD on the platform PL, so that the stability and efficiency in the capturing of the fundus images are improved.

The camera system 10' may further include an actuator MT connected to the supporting portion BSP. The actuator MT drives the camera unit 100 and the optical lens 130 to different angles (as shown in FIG. 5B) so that fundus images of the user UR can be captured from these different angles. For example, the fundus image 400 of the user UR captured from the angle illustrated in FIG. 5A can be the fundus image 400M in FIG. 1B, and the fundus image 400 of the user UR captured from the angle illustrated in FIG. 5B can be the fundus image 400S in FIG. 1C. To be specific, the platform PL can continuously move from one end of the track BSV to the other end thereof, and a plurality of fundus images 400 is continuously captured during the course of the movement. In other words, fundus images 400 of the user UR can be conveniently and accurately captured from different angles by moving the platform PL along the track BSV. Thus, a fundus image 400 of a wider viewing angle can be obtained by a single shooting action. Besides, the white balance values and exposure values of the fundus images 400 are close to each other. Accordingly, the subsequent image stitching operation and clinical diagnosis are made convenient. Meanwhile, repeated shooting actions on the fundus of the user UR are avoided so that the user UR won't feel fatigued to even cause nystagmus that affects the images more, and the medical efficiency and image quality can be improved.

Figure 6A:
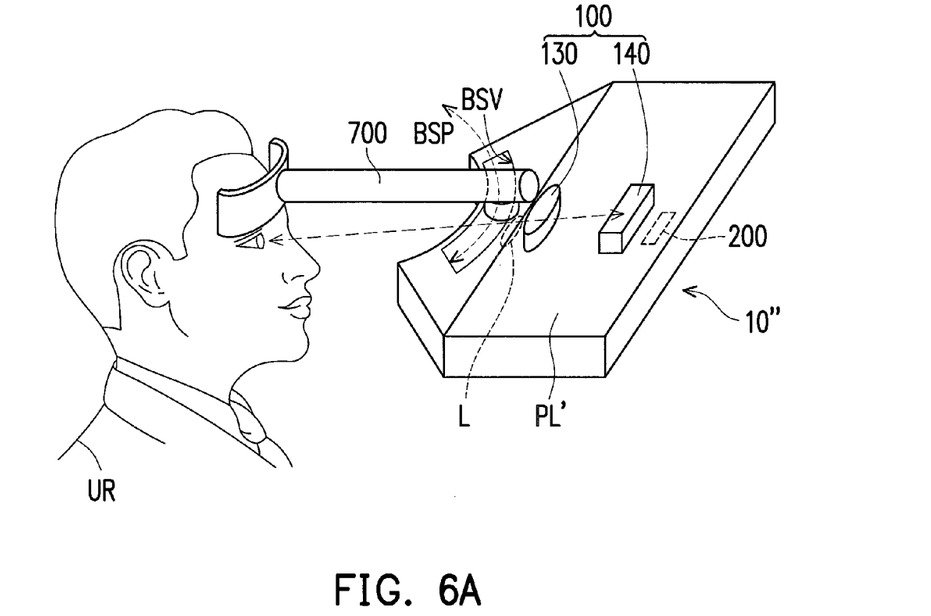
FIG. 6A is a diagram of a camera system according to yet another embodiment of the invention.
Figure 6B:
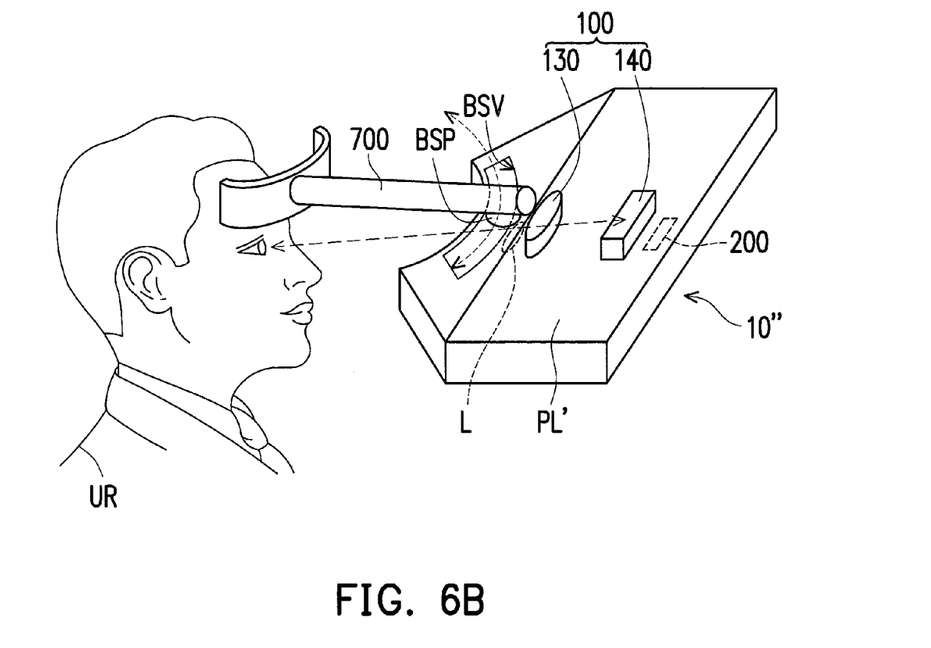
FIG. 6B is a diagram illustrating the operation of the camera system in FIG. 6A.

FIG. 6A is a diagram of a camera system according to yet another embodiment of the invention. FIG. 6B is a diagram illustrating the operation of the camera system in FIG. 6A. Referring to FIG. 6A and FIG. 6B, the camera system in the present embodiment has a structure similar to that in the embodiment illustrated in FIG. 5A. The difference between the present embodiment and the embodiment in FIG. 5A is that in the camera system 10" illustrated in FIG. 6A, the camera unit 100 and the optical lens 130 are disposed in the platform PL' and the platform PL' has a track BSV. The user UR can lean his or her face on the supporting element 700, so that the platform PL' can change the shooting angle relative to the face of the user UR through the track BSV. Thereby, the same function as that of the camera system 10' in the embodiment illustrated in FIG. 5A can be achieved. However, the positions, shapes, structures, and operations of the elements in the camera systems described above are only examples for describing the embodiments of the invention but not intended to limit the scope of the invention, and which can be changed according to the actual design requirement.

As described above, in an image stitching method provided by an embodiment of the invention, fundus images of an animal are captured from different angles, and the fundus images are then converted into grayscale images. After that, the grayscale images are enhanced, and stitching data between the grayscale images is calculated. By converting the fundus images into the grayscale images, the time for stitching the images is shortened and the efficiency and accuracy in stitching the fundus images are improved. In addition, by bringing the stitching data between the enhanced grayscale images back into the full-color fundus images corrected according to the optical parameter of an optical lens, the images stitching operation won't be affected by the color of the images, so that the quality of the stitched image can be improved (for example, the stitching of retinal capillaries and the image contrast can be improved). Moreover, in a camera system provided by an embodiment of the invention, images of different areas on the fundus can be quickly and continuously captured from different angles, so that a full-color fundus image having a wider viewing angle compared to that of a fundus image captured in a single shooting action can be obtained. Particularly, the fundus image can contain image of the macula or the optic disc to facilitate the clinical diagnosis of any eye disease.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. An image stitching method, adapted to stitch a plurality of images of a fundus of an eye of an animal, the image stitching method comprising:
 capturing a plurality of fundus images of the eye of the animal, wherein the fundus images partially overlap;
 respectively converting the fundus images into a plurality of grayscale images;
 enhancing contrasts of the grayscale images;
 comparing the grayscale images with the enhanced contrasts to obtain a plurality of stitching data; and
 stitching the fundus images according to the stitching data.

2. The image stitching method according to claim 1, wherein the step of capturing the fundus images comprises capturing the fundus images by using an optical lens, and the image stitching method further comprises:
 before respectively converting the fundus images into the grayscale images, correcting the fundus images according to an optical parameter of the optical lens, wherein the step of respectively converting the fundus images into the grayscale images comprises respectively converting the corrected fundus images into the grayscale images.

3. The image stitching method according to claim 2, wherein the step of correcting the fundus images comprises diminishing pincushion distortion of the fundus images.

4. The image stitching method according to claim 1, wherein the fundus images are color images.

5. The image stitching method according to claim 1, wherein the step of enhancing the contrast of each of the grayscale images comprises:
 calculating a grayscale distribution relation between a pixel number and a grayscale value in the grayscale image;
 serving a grayscale range corresponding to a section having a greatest continuous slope variation in the grayscale distribution relation as a pending grayscale range;
 determining a converting relation between the pending grayscale range and a contrast-enhanced grayscale range, wherein a lower limit of the contrast-enhanced grayscale range is smaller than a lower limit of the pending grayscale range, and an upper limit of the contrast-enhanced grayscale range is greater than an upper limit of the pending grayscale range; and
 respectively converting a plurality of grayscale values corresponding to the pending grayscale range in the grayscale image into a plurality of grayscale values of the contrast-enhanced grayscale range according to the converting relation.

6. The image stitching method according to claim 1, wherein the step of comparing the grayscale images with the enhanced contrasts to obtain the stitching data comprises:
 executing a planar surface stitching algorithm on the grayscale images with the enhanced contrasts to calculate the stitching data, wherein the stitching data comprises a plurality of stitching data respectively corresponding to the fundus images.

7. The image stitching method according to claim 1, wherein at least a part of the fundus images comprises at least one of an optic disc image, a macula image, and a blood vessel image, and the step of comparing the grayscale images with the enhanced contrasts to obtain the stitching data comprises comparing a part of the grayscale images with the enhanced contrasts corresponding to at least one of the optic disc image, the macula image, and the blood vessel image on a first priority to obtain the stitching data.

8. The image stitching method according to claim 1, wherein the step of capturing the fundus images of the animal comprises capturing the fundus images of the animal from a plurality of different angles.

9. A camera system, adapted to obtaining an image of a fundus of an eye of an animal, the camera system comprising:
a camera unit, capturing a plurality of fundus images of the eye of the animal, wherein the fundus images partially overlap; and
a processing unit, electrically connected with the camera unit, wherein the processing unit respectively converts the fundus images into a plurality of grayscale images, the processing unit enhances contrasts of the grayscale images, the processing unit compares the grayscale images with the enhanced contrasts to obtain a plurality of stitching data, and the processing unit stitches the fundus images according to the stitching data.

10. The camera system according to claim 9, wherein the camera unit comprises an optical lens and an image sensor, the camera unit aims at the fundus of the eye of the animal from a plurality of different angles, so that the optical lens projects the fundus on the image sensor from the different angles so that the image sensor respectively captures the fundus images.

11. The camera system according to claim 10 further comprising an actuator, wherein the actuator is connected to the camera unit and configured to move the camera unit to the different angles.

12. The camera system according to claim 10, wherein the processing unit corrects the fundus images according to an optical parameter of the optical lens and then respectively converts the corrected fundus images into the grayscale images.

13. The camera system according to claim 12, wherein the processing unit diminishes pincushion distortion of the fundus images according to the optical parameter of the optical lens.

14. The camera system according to claim 9, wherein the fundus images are color images.

15. The camera system according to claim 9, wherein the processing unit calculates a grayscale distribution relation between a pixel number and a grayscale value in each of the grayscale images, the processing unit serves a grayscale range corresponding to a section having a greatest continuous slope variation in the grayscale distribution relation as a pending grayscale range, the processing unit determines a converting relation between the pending grayscale range and a contrast-enhanced grayscale range, a lower limit of the contrast-enhanced grayscale range is smaller than a lower limit of the pending grayscale range, an upper limit of the contrast-enhanced grayscale range is greater than an upper limit of the pending grayscale range, and the processing unit respectively converts a plurality of grayscale values corresponding to the pending grayscale range in the grayscale image into a plurality of grayscale values of the contrast-enhanced grayscale range according to the converting relation.

16. The camera system according to claim 9, wherein the processing unit executes a planar surface stitching algorithm on the grayscale images with the enhanced contrasts to calculate the stitching data, wherein the stitching data comprises a plurality of stitching data respectively corresponding to the fundus images.

17. The camera system according to claim 9, wherein at least a part of the fundus images comprises at least one of an optic disc image, a macula image, and a blood vessel image, and the processing unit compares a part of the grayscale images with the enhanced contrasts corresponding to at least one of the optic disc image, the macula image, and the blood vessel image on a first priority to obtain the stitching data.

18. The camera system according to claim 9 further comprising an illumination light source for providing an illumination beam to the fundus of the eye of the animal, wherein the fundus reflects the illumination beam into a plurality of image beams respectively carrying the fundus images, and the camera unit is respectively disposed on light paths of the image beams at a plurality of different time points for capturing the fundus images.

* * * * *